United States Patent [19]

Hoffmann et al.

[11] Patent Number: 4,820,862

[45] Date of Patent: * Apr. 11, 1989

[54] PROCESS FOR THE PREPARATION OF DIMETHYL TEREPHTHALATE

[75] Inventors: Gerhart Hoffmann, Ranzel-Kolonie, Fed. Rep. of Germany; Karl Irlweck, Vienna, Austria; Rudolf Cordes, Ranzel, Fed. Rep. of Germany

[73] Assignee: Dynamit Nobel Aktiengesellschaft, Troisdorf, Fed. Rep. of Germany

[*] Notice: The portion of the term of this patent subsequent to Aug. 24, 1999 has been disclaimed.

[21] Appl. No.: 630,264

[22] Filed: Jul. 12, 1984

Related U.S. Application Data

[63] Continuation of Ser. No. 121,151, Mar. 4, 1971, abandoned.

[30] Foreign Application Priority Data

Mar. 4, 1970 [DE] Fed. Rep. of Germany ....... 2010137

[51] Int. Cl.$^4$ .................... C07C 67/39; C07C 67/08
[52] U.S. Cl. .................... 560/77; 502/171; 502/324; 502/326; 560/99; 562/412; 562/414
[58] Field of Search .................... 560/77, 99; 562/412, 562/414; 502/171, 324, 326

[56] References Cited

U.S. PATENT DOCUMENTS

| | | | |
|---|---|---|---|
| 2,245,528 | 6/1941 | Loder | 560/417 |
| 2,723,994 | 11/1958 | Harfele et al. | 562/412 |
| 2,833,816 | 5/1958 | Saffer et al. | 560/77 X |
| 2,880,237 | 3/1959 | Knoblach | 560/77 X |
| 2,894,978 | 7/1959 | Katzschmann | 560/412 X |
| 4,346,230 | 8/1982 | Hoffmann et al. | 560/99 |

FOREIGN PATENT DOCUMENTS

| | | |
|---|---|---|
| 747952 | 12/1966 | Canada . |
| 949564 | 8/1956 | Fed. Rep. of Germany . |
| 1041945 | 10/1958 | Fed. Rep. of Germany . |
| 1114472 | 10/1962 | Fed. Rep. of Germany . |
| 1251735 | 10/1967 | Fed. Rep. of Germany . |
| 37-14804 | 9/1962 | Japan . |
| 43-9739 | 4/1968 | Japan . |
| 815198 | 6/1959 | United Kingdom . |
| 857098 | 12/1960 | United Kingdom . |

*Primary Examiner*—Werren B. Lone
*Assistant Examiner*—Vera C. Clarke
*Attorney, Agent, or Firm*—Antonelli, Terry & Wands

[57] ABSTRACT

The yield of dimethyl terephthalate obtained by the oxidation of a mixture of p-xylene and methyl p-toluate, preferably with air, and esterification of the thus-produced acids is increased by utilizing a mixture of cobalt and manganese compounds as the oxidation catalyst.

6 Claims, No Drawings

PROCESS FOR THE PREPARATION OF DIMETHYL TEREPHTHALATE

This is a continuation of application Ser. No. 121,151 filed Mar. 4, 1971, now abandoned.

BACKGROUND OF THE INVENTION

This invention relates to an improved process for the preparation of dimethyl terephthalate. More particularly, it relates to a catalyst system of higher selectivity for the air oxidation of p-xylene/p-toluic acid methyl ester mixtures, for example, in accordance with German Pat. Nos. 949,564 and 1,041,945.

Dimethyl terephthalate is produced in numerous large-scale industrial plants in accordance with the "Katzschmann process", described in said patents. The principle of this process resides in that the p-toluic acid, which first evolves during the catalytic air oxidation of p-xylene in the liquid phase, is esterified with methanol, and the resultant methyl p-toluate is again recycled into the oxidation stage and is oxidized to monomethyl terephthalate. In practice, the process is conducted in such a manner that methyl p-toluate and p-xylene are oxidized with air together with cobalt salts soluble in the reaction medium, in a batch-wise or continuous fashion, and the thus-obtained acids are esterified with methanol. The mixture, consisting mainly of dimethyl terephthalate and methyl p-toluate, is then worked up, preferably by distillation, and the thus-obtained methyl p-toluate is recycled to the oxidation stage.

Numerous catalysts have been described for the air oxidation of alkyl aromatics, especially of p-xylene. These catalysts make it possible to effect, by increased activity, the direct oxidation up to terephthalic acid during the air oxidation of p-xylene conducted in the present of aliphatic lower monocarboxylic acids, which normally leads only to p-toluic acid. The increased activity is attained, for example, by adding $Br^-$ to cobalt- and manganese-containing catalysts. In the Katzschmann process for the production of dimethyl terephthalate, an increased activity of the catalyst is of minor importance, since the oxidation of p-xylene proceeds via the intermediate stage of methyl p-toluate with a sufficient speed to monomethyl terephthalate. In this connection, it is rather the selectivity of the catalyst which is of interest, i.e., the yield of dimethyl terephthalate. No catalyst systems have been known or reported heretofore which result in a higher selectivity or improved yields of dimethyl terephthalate in connection with the Katzschmann process, as compared to the generally employed cobalt catalyst. In addition to cobalt salts, salts of a great variety of metals have been examined with respect to their catalytic effect for conducting this process, for example, manganese, chromium, cerium and lead salts. These salts, however, exhibit a less favorable effectiveness [Katzschmann, "A Process for the Oxidation of Alkyl Aromatics", Chemie-Ingenieur-Technik (Chemical Engineering Technology), Vol. 38, 1966, pp. 1–10].

When juding the selectivity of an oxidation catalyst, consideration can be based on the fact that the main reaction in the reaction fundamental to the Katzschmann process, i.e., the oxidation of the alkyl groups of xylene and methyl p-toluate, can be controlled, observed or monitored approximately by the acid number of the reaction mixture, whereas the secondary reactions are indicated by the formation of $CO_2$, $CO$, formic acid, acetic acid and higher molecular weight condensation products. Other yield determinations do not result in accurate data in experimental oxidations, because of the complicated nature of the composition of the reaction products.

Accordingly, one of the objects of the present invention is to provide a process for the preparation of dimethyl terephthalate which gives improved results over the prior art.

Another object of the present invention is to provide a catalyst system of high selectivity for obtaining high yields of dimethyl terephthalate.

A further object of the invention is to provide a process for the preparation of dimethyl terephthalate which may be carried out advantageously and efficaciously on an industrial scale to give a high yield of product.

These and other objects and advantages of the present invention will become apparent to those skilled in the art from a consideration of the following specification and claims.

SUMMARY OF THE INVENTION

In accordance with the present invention, it has been found that a higher yield of dimethyl terephthalate can be obtained when a mixed catalyst containing cobalt and manganese is employed, because of the fact that such a catalyst develops a higher selectivity to the effect that the formation of by-products is extensively diminished. In experiments carried out with regard to this point, wherein the by-products were accurately determined, it was found that the yields of formic acid and acetic acid, when using $Co^{++}$ and $Mn^{++}$ as the catalyst, differ essentially from each other. When employing cobalt, approximately 2 moles of acetic acid are formed per 1 mole of formic acid, whereas, in the case of manganese, formic acid is mainly produced and only a small amount of acetic acid is obtained. In both cases, the entire yield losses are approximately the same. When employing manganese compounds or mixtures of cobalt compounds and manganese compounds as the catalyst, the start-up of the oxidation reaction is, in most instances, somewhat delayed as compared to cobalt. Therefore, it proved to be particularly advantageous, when conducting the oxidation with a cobalt-manganese mixed catalyst, to effect the starting reaction with $Co^{++}$ by itself and, thereafter, to add the manganese catalyst thereto. The advantageous effect of the combination of cobalt and manganese on the selectivity of the course of the reaction is, however, present in any event.

By the use of the cobalt-manganese mixed catalyst in accordance with this invention, the formation of $CO_2$ and acetic acid, in particular, is substantially reduced. The yield of higher condensation compounds was approximately the same with the catalysts tested.

If the oxidation is conducted batch-wise, it is advantageous to add first, in a conventional manner, the cobalt catalyst in an amount of 0.005–1% by weight, preferably 0.005–0.05% by weight. About 15 minutes to several hours after the start of the reaction, the manganese catalyst is then added in an amount of 0.005–1% by weight, preferably 0.005–0.05% by weight. When effecting a continuous oxidation, it may be advantageous in connection with the process of this invention to conduct the reaction in 2–4 stages, and to feed the cobalt catalyst continuously into the first stage and the manganese catalyst continuously into the second, third or fourth stage. However, it is, of course, also possible to add the catalyst mixture in the first stage only or to add $Co^{++}$ and/or $Mn^{++}$ in different concentrations to several stages of the oxidation. It is also feasible to conduct the process in a single stage.

The catalysts are normally introduced into the oxidation system in the form of salts which are soluble in the reaction medium. For example, it is possible to utilize the salts of higher molecular weight fatty acids, naphthenic acids and aromatic carboxylic acids. However, it is also possible, especially when the oxidation is conducted continuously, to employ aqueous solutions of cobalt and manganese salts or suspensions of finely divided oxides or hydroxides of the metals.

EXAMPLES OF THE INVENTION

The following examples are given merely as illustrative of the present invention and are not to be considered as limiting.

EXAMPLE 1

In a glass jar having a height of 150 cm. and a diameter of 5 cm. are charged 330 g. of xylene, 670 g. of methyl p-toluate and 100 mg. of $Co^{++}$ or $Mn^{++}$ in the form of a 3% xylenic solution of the ethyl hexanoic acid salt. The mixture is heated under a pressure of 1 atmosphere to 140° C., and air is introduced thereto at a rate of 1.5 liters per minute. In the experiments with the cobalt-manganese catalyst, 100 mg. of manganese is added 1 hour after the start-up of the reaction in the form of a 3% xylenic solution of the ethyl hexanoic acid salt. The exhausted air is conducted over a reflux condenser, and the thus-obtained condensate is separated into water and organic components. The organic components flow back into the reaction vessel, whereas the aqueous phase is withdrawn and analyzed with respect to formic and acetic acid. Furthermore, the amount of $CO_2$ present in the waste air is determined. After 6 hours, the reaction is terminated, and the final acid number of the reaction mixture is determined. Table 1 shows the results of these experiments.

TABLE 1

| Experiment No. | Catalyst | Final Acid Number | Carbon Losses (millimoles) | | |
|---|---|---|---|---|---|
| | | | Formic Acid | Acetic Acid | $CO_2$ | Total |
| 1 | 100 mg. $Co^{++}$ | 90.3 | 11.7 | 21.2 | 20.9 | 75.0 |
| 2 | | 83.7 | 10.5 | 21.3 | 16.0 | 69.1 |
| 3 | | 83.2 | 14.5 | 20.2 | 20.5 | 75.4 |
| 4 | | 81.5 | 11.8 | 17.9 | 16.3 | 63.9 |
| | | 84.7 | 12.1 | 20.1 | 18.4 | 70.9 |
| 5 | 100 mg. $Mn^{++}$ | 85.4 | 27.8 | 4.0 | 33.3 | 69.1 |
| 6 | | 86.2 | 25.6 | 6.6 | 33.8 | 72.5 |
| 7 | | 87.0 | 26.4 | 5.9 | 34.2 | 72.4 |
| 8 | | 85.9 | 24.9 | 5.6 | 32.9 | 69.0 |
| | | 86.1 | 26.2 | 5.5 | 33.6 | 70.7 |
| 9 | 100 mg. $Co^{++}$ + | 80.1 | 16.1 | 10.0 | 15.4 | 51.5 |
| 10 | 100 mg. $Mn^{++}$ | 90.9 | 21.7 | 9.8 | 14.8 | 56.1 |
| 11 | | 87.6 | 19.9 | 9.2 | 16.6 | 54.9 |
| 12 | | 89.4 | 17.9 | 10.7 | 17.1 | 56.4 |
| | | 87.0 | 18.9 | 9.9 | 16.0 | 54.7 |

EXAMPLE 2

Into a reactor made of stainless steel with a capacity of 1.5 m$^3$, equipped with an air feeding pipe, a heating and cooling system, a vapor condenser and a reaction water separator, are charged 400 liters of xylene and 3.5 liters of a 3% xylenic solution of ethyl hexanoic acid $Co^{++}$ salt. Thereafter, the mixture is heated to 150° C., and 30 Nm$^3$ (a volumetric quantity based on 0° C. and 1 atmosphere absolute) per hour of air is introduced thereto. The pressure is adjusted to 6 atmospheres. After the reaction has started, 600 liters of methyl p-toluate is introduced within one hour; at the same time, the amount of air is increased to 60 Nm$^3$ per hour. In experiments with the cobalt-manganese catalyst, 3.5 liters of a 3% xylenic solution of the $Mn^{++}$ salt of ethyl hexanoic acid is added after termination of the feeding of the methyl p-toluate. The water of reaction and the exhaust air are analyzed, in accordance with the procedure described in Example 1, with respect to formic and acetic acid or $CO_2$ and CO. Furthermore, the acid number of the reaction mixture is determined. After 10 hours, the reaction is terminated. Table 2 shows the results of these experiments.

TABLE 2

| Experiment No. | Catalyst | Final Acid Number | Carbon Losses (moles) | | | |
|---|---|---|---|---|---|---|
| | | | Formic Acid | Acetic Acid | $CO_2$ + CO | Total |
| 1 | Cobalt | 242 | 41 | 44 | 620 | 749 |
| 2 | | 232 | 34 | 39 | 623 | 735 |
| 3 | Cobalt + | 255 | 37 | 26 | 447 | 536 |
| 4 | Manganese | 245 | 39 | 19 | 440 | 517 |

The formation of higher molecular weight compounds and other byproducts is, on the average, 1.7% in experiments 1 and 2 and, on the average, 1.9% in experiments 3 and 4.

The invention being thus described, it will be obvious that the same may be varied in many ways. Such variations are not to be regarded as a departure from the spirit and scope of the invention, and all such modifications as would be obvious to one skilled in the art are intended to be included herein.

We claim:

1. In a process for the preparation of dimethyl terephthalate by the air oxidation of a mixture of p-xylene and methyl p-toluate, in the presence of an oxidation catalyst at a temperature of from about 80° to about 250° C., esterification of the thus-produced acids and recycling of the methyl p-toluate into the oxidation step, the improvement which comprises utilizing a mixture of cobalt and manganese compounds as the oxidation catalyst to improve the yield of dimethyl terephthalate, said compounds being soluble in the reaction medium used, being water soluble salts, or being oxides and hydroxides, the cobalt concentration in the reaction medium and the manganese concentration in the reaction medium being in a ratio of from 1:1 to 10:1.

2. A process in accordance with claim 1, wherein said cobalt and manganese compounds are salts of cobalt and manganese which are soluble in the reaction medium.

3. A process in accordance with claim 2, wherein said cobalt and manganese compounds are the cobalt and manganese salts of higher molecular weighty fatty acids, naphthenic acids and aromatic carboxylic acids.

4. A process in accordance with claim 1, wherein said cobalt and manganese compounds are oxides or hydroxides of cobalt and manganese.

5. A process in accordance with claim 1, wherein said oxidation catalyst is a mixture of the ethyl hexanoic acid salts of cobalt and of manganese.

6. In a process for the preparation of dimethyl terephthalate by the air oxidation of a mixture of p-xylene and methyl p-toluate, in the presence of from 0.001% to about 0.1% by weight of an oxidation catalyst at a temperature from about 80° to about 250° C., esterification of the thus-produced acids and recycling of the methyl p-toluate into the oxidation step, the improvement which comprises utilizing a mixture of cobalt and manganese compounds as the oxidation catalyst to improve the yield of dimethyl terephthalate, said compounds being soluble in the reaction medium being used, being water soluble salts or being oxides or hydroxides, and the ratio of the cobalt concentration to the manganese concentration in the reaction medium being from about 1:1 to 10:1.

* * * * *